US010413497B2

(12) United States Patent
Yang et al.

(10) Patent No.: US 10,413,497 B2
(45) Date of Patent: *Sep. 17, 2019

(54) HAIR CONDITIONING COMPOSITION HAVING HIGHER YIELD POINT AND HIGHER CONVERSION RATE OF FATTY COMPOUND TO GEL MATRIX (71) Applicant: The Procter & Gamble Company, Cincinnati, OH (US)

(72) Inventors: Jian-Zhong Yang, Kobe (JP); Toshiyuki Okada, Singapore (SG)

(73) Assignee: The Procter and Gamble Company, Cincinnati, OH (US)

( * ) Notice: Subject to any disclaimer, the term of this patent is extended or adjusted under 35 U.S.C. 154(b) by 89 days.

This patent is subject to a terminal disclaimer.

(21) Appl. No.: 14/462,131

(22) Filed: Aug. 18, 2014

(65) Prior Publication Data
US 2014/0356307 A1  Dec. 4, 2014

Related U.S. Application Data (60) Continuation of application No. 13/525,691, filed on Jun. 18, 2012, now Pat. No. 8,828,370, which is a division of application No. 12/491,478, filed on Jun. 25, 2009, now abandoned.

(60) Provisional application No. 61/133,002, filed on Jun. 25, 2008.

(51) Int. Cl.
A61Q 5/12 (2006.01)
A61K 8/41 (2006.01)
A61K 8/34 (2006.01)
A61K 8/42 (2006.01)
A61K 8/58 (2006.01)
A61K 8/73 (2006.01)

(52) U.S. Cl.
CPC ............. A61K 8/416 (2013.01); A61K 8/34 (2013.01); A61K 8/342 (2013.01); A61K 8/42 (2013.01); A61K 8/585 (2013.01); A61K 8/731 (2013.01); A61Q 5/12 (2013.01); A61K 2800/48 (2013.01); A61K 2800/805 (2013.01)

(58) Field of Classification Search
None
See application file for complete search history.

(56) References Cited

U.S. PATENT DOCUMENTS

| 3,249,550 | A |  | 5/1966 | Metters |
| 3,616,859 | A |  | 11/1971 | Shay et al. |
| 4,024,078 | A |  | 5/1977 | Gilbert et al. |
| 4,294,728 | A |  | 10/1981 | Vanlerberghe et al. |
| 4,753,754 | A |  | 6/1988 | Messenger |
| 4,980,078 | A |  | 12/1990 | Verite et al. |
| 5,077,042 | A |  | 12/1991 | Darkwa et al. |
| 5,213,793 | A | * | 5/1993 | Moses ............... A61K 8/416 |
|  |  |  |  | 132/202 |
| RE34,584 | E |  | 4/1994 | Grote |
| 5,440,032 | A |  | 8/1995 | Hirosawa et al. |
| 5,482,543 | A |  | 1/1996 | Bleve et al. |
| 5,580,850 | A |  | 12/1996 | Bigorra |
| 5,610,127 | A |  | 3/1997 | Erilli et al. |
| 5,635,466 | A |  | 6/1997 | Burdon et al. |
| 5,695,748 | A |  | 12/1997 | Francis |
| 5,741,948 | A |  | 4/1998 | Kirishiki et al. |
| 5,750,099 | A |  | 5/1998 | Yoshihara et al. |
| 5,814,323 | A |  | 9/1998 | Lyle |
| 5,906,972 | A |  | 5/1999 | Gabriel et al. |
| 5,942,485 | A |  | 8/1999 | Kemen |
| 5,958,868 | A |  | 9/1999 | Pi Subirana et al. |
| 5,994,595 | A |  | 11/1999 | Onda et al. |
| 6,074,633 | A |  | 6/2000 | Dubief et al. |
| 6,150,322 | A |  | 11/2000 | Singleton et al. |
| 6,207,626 | B1 |  | 3/2001 | Gonzalez et al. |
| 6,399,045 | B1 |  | 6/2002 | Morgan et al. |
| 6,417,408 | B2 |  | 7/2002 | Onda et al. |
| 6,432,420 | B2 |  | 8/2002 | Ellis et al. |
| 6,471,953 | B1 |  | 10/2002 | N'Guyen et al. |

(Continued)

FOREIGN PATENT DOCUMENTS

DE  19534372 A1  9/1995
EP  336803 B1  9/1992

(Continued)

OTHER PUBLICATIONS

Bran Luebbe, "Continuous Dilution of Concentrated Alkyl Ether Sulfates", vol. 103-No. 16/1977, 465-466.
XP002545441, Thomson, 1 page.
XP002545442, Thomson, 1 page.
PCT International Search Report for PCT/US2009/048533 dated Dec. 3, 2010, 6 pages.
Hong, J.E. et al, "Hair conditioner composition containing polyalcohol as active ingredient for improving hair volume without sticky feeling", vol. 2007, No. 21, Oct. 9, 2006, abstract.
Hong, J.E. et al., "Hair conditioner composition", vol. 2005, No. 9, Sep. 4, 2004, abstract.

(Continued)

Primary Examiner — Jyothsna A Venkat
(74) Attorney, Agent, or Firm — Alexandra S. Anoff (57) ABSTRACT Disclosed is a hair conditioning composition comprising: (a) a cationic surfactant; (b) a high melting point fatty compound; and (c) an aqueous carrier; wherein the cationic surfactant, the high melting point fatty compound, and the aqueous carrier form a gel matrix; wherein the composition has from about 90% to about 100% of a conversion rate of the high melting point fatty compound to the gel matrix; and wherein the composition has a yield point of about 33 Pa or more. Also disclosed is a method of manufacturing of hair conditioning composition. The compositions of the present invention, and the compositions made by the method of the present invention, provide improved conditioning benefits, especially, improved wet conditioning benefits after rinsing and improved dry conditioning, while maintaining wet conditioning benefit before rinsing.

10 Claims, 1 Drawing Sheet

(56) References Cited

U.S. PATENT DOCUMENTS

| | | |
|---|---|---|
| 6,607,715 B1 | 8/2003 | Barinova et al. |
| 6,706,931 B2 | 3/2004 | Edwards |
| 6,730,292 B1 | 5/2004 | Yang et al. |
| 6,849,252 B1 | 2/2005 | Yang |
| 6,884,275 B2 | 4/2005 | Okada et al. |
| 6,946,122 B2 | 9/2005 | Yang |
| 6,946,437 B2 | 9/2005 | Aizawa et al. |
| 7,208,480 B2 | 4/2007 | Williams et al. |
| 7,666,825 B2 | 2/2010 | Wagner et al. |
| 8,349,301 B2 | 1/2013 | Wells et al. |
| 8,349,302 B2 | 1/2013 | Johnson et al. |
| 8,361,448 B2 | 1/2013 | Johnson et al. |
| 8,361,449 B2 | 1/2013 | Wells et al. |
| 8,361,450 B2 | 1/2013 | Johnson et al. |
| 8,367,048 B2 | 2/2013 | Wells et al. |
| 8,470,305 B2 | 6/2013 | Johnson et al. |
| 8,828,370 B2 * | 9/2014 | Yang et al. ................. 424/70.27 |
| 9,381,382 B2 | 7/2016 | Schwartz et al. |
| 2002/0041854 A1 | 4/2002 | Hadasch et al. |
| 2002/0110533 A1 * | 8/2002 | Huff et al. .................... 424/70.1 |
| 2002/0122772 A1 | 9/2002 | Lukenbach et al. |
| 2002/0151738 A1 | 10/2002 | Edwards |
| 2003/0083210 A1 | 5/2003 | Goldberg et al. |
| 2003/0223952 A1 | 12/2003 | Wells et al. |
| 2003/0224954 A1 | 12/2003 | Wells et al. |
| 2004/0092413 A1 | 5/2004 | Ticktin |
| 2004/0116539 A1 | 6/2004 | Biercevicz |
| 2004/0157754 A1 | 8/2004 | Geary et al. |
| 2004/0166071 A1 | 8/2004 | Pfaffernoschke et al. |
| 2004/0166074 A1 | 8/2004 | Darkwa |
| 2004/0235689 A1 | 11/2004 | Sakai et al. |
| 2004/0254253 A1 | 12/2004 | Culeron |
| 2004/0266652 A1 | 12/2004 | Brown et al. |
| 2004/0266656 A1 | 12/2004 | Sakurai |
| 2005/0063934 A1 | 3/2005 | Baker |
| 2005/0112074 A1 | 5/2005 | Arai et al. |
| 2005/0112083 A1 | 5/2005 | Wells et al. |
| 2005/0166338 A1 | 8/2005 | Arango |
| 2005/0192196 A1 | 9/2005 | Hutton |
| 2005/0241076 A1 | 11/2005 | Bureiko et al. |
| 2005/0255627 A1 | 11/2005 | Omori |
| 2006/0024256 A1 | 2/2006 | Wells |
| 2006/0078528 A1 | 4/2006 | Yang et al. |
| 2006/0078529 A1 * | 4/2006 | Uchida .................. A61K 8/342 424/70.28 |
| 2006/0083703 A1 | 4/2006 | Torgerson |
| 2006/0083704 A1 | 4/2006 | Torgerson |
| 2006/0128596 A1 | 6/2006 | Koshti et al. |
| 2006/0251605 A1 | 11/2006 | Belmar et al. |
| 2006/0286060 A1 | 12/2006 | Yang |
| 2007/0014823 A1 | 1/2007 | Iwata |
| 2007/0041929 A1 * | 2/2007 | Torgerson .............. A61K 8/342 424/70.122 |
| 2007/0119864 A1 | 5/2007 | Tsai |
| 2007/0215642 A1 | 9/2007 | Van Der Heijden |
| 2007/0286837 A1 | 12/2007 | Torgerson |
| 2008/0039352 A1 | 2/2008 | Wells et al. |
| 2008/0139434 A1 | 6/2008 | Basappa et al. |
| 2008/0153730 A1 | 6/2008 | Tsaur et al. |
| 2009/0155383 A1 | 6/2009 | Kitko |
| 2009/0221463 A1 | 9/2009 | Kitko |
| 2009/0227482 A1 | 9/2009 | Dong et al. |
| 2009/0324527 A1 | 12/2009 | Okada et al. |
| 2009/0324528 A1 | 12/2009 | Okada |
| 2009/0324529 A1 | 12/2009 | Okada |
| 2009/0324530 A1 | 12/2009 | Yang et al. |
| 2009/0324531 A1 | 12/2009 | Okada |
| 2009/0324532 A1 | 12/2009 | Okada |
| 2010/0013947 A1 | 1/2010 | Oikawa |
| 2010/0061952 A1 | 3/2010 | Wells et al. |
| 2010/0143280 A1 | 6/2010 | Yokogi |
| 2010/0143281 A1 | 6/2010 | Okada |
| 2010/0143282 A1 | 6/2010 | Yokogi |
| 2010/0143425 A1 | 6/2010 | Okada |
| 2011/0048449 A1 | 3/2011 | Hutton |
| 2011/0053826 A1 | 3/2011 | Wise |
| 2012/0164198 A1 | 6/2012 | Johnson et al. |
| 2014/0356307 A1 | 12/2014 | Yang et al. |

FOREIGN PATENT DOCUMENTS

| | | |
|---|---|---|
| EP | 0573329 B1 | 7/1997 |
| EP | 0834307 A2 | 4/1998 |
| EP | 1009787 B1 | 6/2000 |
| EP | 1696023 B1 | 4/2008 |
| EP | 1572333 B1 | 5/2008 |
| JP | 56001895 A | 1/1981 |
| JP | 58006209 A | 1/1983 |
| JP | 63143935 A2 | 6/1988 |
| JP | 6107888 | 4/1994 |
| JP | 07034089 A | 2/1995 |
| JP | 09249900 A | 9/1997 |
| JP | 2002038200 | 2/2002 |
| JP | 2003205039 | 7/2003 |
| JP | 2005113067 A | 4/2005 |
| JP | 2005232118 | 9/2005 |
| JP | 2005255627 A2 | 9/2005 |
| WO | WO98/57615 | 12/1998 |
| WO | WO99/62492 A1 | 12/1999 |
| WO | WO9962492 A1 | 12/1999 |
| WO | WO0000170 | 1/2000 |
| WO | WO0040213 A1 | 7/2000 |
| WO | WO0117492 A1 | 3/2001 |
| WO | WO04054693 A1 | 7/2004 |
| WO | WO2005070374 A1 | 8/2005 |
| WO | WO2005074868 A1 | 8/2005 |
| WO | WO2010052092 A1 | 5/2010 |

OTHER PUBLICATIONS

"Yield Point", Collins English Dictionary, Harper Collins Publishers 2000.
All Final and Non-Final Office Actions for U.S. Appl. No. 12/491,478.
All Final and Non-Final Office Actions for U.S. Appl. No. 12/491,489.
All Final and Non-Final Office Actions for U.S. Appl. No. 12/491,501.
All Final and Non-Final Office Actions for U.S. Appl. No. 12/491,518.
All Final and Non-Final Office Actions for U.S. Appl. No. 12/491,545.
All Final and Non-Final Office Actions for U.S. Appl. No. 12/491,560.
All Final and Non-Final Office Actions for U.S. Appl. No. 12/633,939.
All Final and Non-Final Office Actions for U.S. Appl. No. 12/633,952.
All Final and Non-Final Office Actions for U.S. Appl. No. 12/633,965.
All Final and Non-Final Office Actions for U.S. Appl. No. 12/633,987.
All Final and Non-Final Office Actions for U.S. Appl. No. 13/525,691.

* cited by examiner

HAIR CONDITIONING COMPOSITION HAVING HIGHER YIELD POINT AND HIGHER CONVERSION RATE OF FATTY COMPOUND TO GEL MATRIX

FIELD OF THE INVENTION

The present invention relates to a hair conditioning composition comprising: (a) a cationic surfactant; (b) a high melting point fatty compound; and (c) an aqueous carrier; wherein the cationic surfactant, the high melting point fatty compound, and the aqueous carrier form a gel matrix; wherein the composition has from about 90% to about 100% of a conversion rate of the high melting point fatty compound to the gel matrix; and wherein the composition has a yield point of about 33 Pa or more. The present invention also relates to a method of manufacturing of hair conditioning composition. The compositions of the present invention, and the compositions made by the method of the present invention, provide improved conditioning benefits, especially, improved wet conditioning benefits after rinsing and improved dry conditioning, while maintaining wet conditioning benefit before rinsing.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits. For example, some cationic surfactants, when used together with some high melting point fatty compounds and aqueous carrier, are believed to provide a gel matrix which is suitable for providing a variety of conditioning benefits such as slippery feel during the application to wet hair and softness and moisturized feel on dry hair.

For example, WO 2006/044209 discloses a hair conditioning composition comprising by weight: (a) from about 0.1% to about 10% of a cationic surfactant; (b) from about 2.5% to about 15% by weight of the composition of a high melting point fatty compound; and (c) and an aqueous carrier; wherein the cationic surfactant, the high melting point fatty compound, and the aqueous carrier form a lamellar gel matrix; wherein the d-spacing of the lamellar layers is in the range of 33 nm or less; and wherein the composition has a yield stress of about 30 Pa or more at 26.7° C. This hair conditioning compositions are said to provide improved conditioning benefits, especially improved slippery feel during the application to wet hair. WO 2006/044209 also describes that; preferably, the composition of the present invention comprises, by weight of the hair care composition, from about 60% to about 99% of a gel matrix including lamellar gel matrix. WO 2006/044209 also describes that; in highly preferred composition, the DSC profile shows a single peak having a peak top temperature of about 67° C. to about 73° C., at about 8 mJ/mg, and no peaks larger than 2 mJ/mg from 40° C. to about 65° C. as the peaks showing at a temperature of from 40° C. to 55° C. mean the existence of high melting fatty compounds and/or cationic surfactants which are not incorporated into the gel matrix.

However, there remains a need for hair conditioning compositions which provide improved conditioning benefits, especially, improved wet conditioning benefits after rinsing and improved dry conditioning, while maintaining wet conditioning benefit before rinsing. Such wet conditioning benefits after rinsing include, for example, reduced friction of wet hair after rinsing and/or easiness to comb wet hair after rinsing.

Additionally, there may exist a need for hair conditioning compositions which provide an improved product appearance, i.e., richer, thicker, and/or more concentrated product appearance, and which consumer may feel higher conditioning benefits from its appearance.

Based on the foregoing, there remains a need for conditioning compositions which provide improved conditioning benefits, especially, improved wet conditioning benefits after rinsing and improved dry conditioning, while maintaining wet conditioning benefit before rinsing. Additionally, there may exist a need for conditioning compositions which provide an improved product appearance.

None of the existing art provides all of the advantages and benefits of the present invention.

SUMMARY OF THE INVENTION

The present invention is directed to a hair conditioning composition comprising:
(a) a cationic surfactant;
(b) a high melting point fatty compound; and
(c) an aqueous carrier;
wherein the cationic surfactant, the high melting point fatty compound, and the aqueous carrier form a gel matrix; wherein the composition has from about 90% to about 100% of a conversion rate of the high melting point fatty compound to the gel matrix; and wherein the composition has a yield point of about 33 Pa or more.

The present invention is also directed to a method of manufacturing a hair conditioning composition, wherein the composition comprises a cationic surfactant, a high melting point fatty compound, and an aqueous carrier; wherein a total amount of the cationic surfactant and the high melting point fatty compound is from about 7.0% to about 15% by weight of the composition; wherein the method comprises the steps:
(1) preparing a premix comprising the cationic surfactants and the high melting point fatty compounds, wherein the temperature of the premix is higher than a melting point of the high melting point fatty compounds; and
(2) preparing an aqueous carrier, wherein the temperature of the aqueous carrier is below the melting point of the high melting point fatty compounds; and
(3) mixing the premix with the aqueous carrier and forming gel matrix.

The compositions of the present invention, and the compositions made by the method of the present invention, provide improved conditioning benefits, especially, improved wet conditioning benefits after rinsing and improved dry conditioning, while maintaining wet conditioning benefit before rinsing.

These and other features, aspects, and advantages of the present invention will become better understood from a reading of the following description, and appended claims.

BRIEF DESCRIPTION OF THE DRAWINGS

While the specification concludes with claims particularly pointing out and distinctly claiming the invention, it is believed that the invention will be better understood from the following description of the accompanying FIGURE in which:

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Composition

The hair conditioning composition of the present invention comprising:
(a) a cationic surfactant;
(b) a high melting point fatty compound; and
(c) an aqueous carrier;
wherein the cationic surfactant, the high melting point fatty compound, and the aqueous carrier form a gel matrix; wherein the composition has from about 90% to about 100% of a conversion rate of the high melting point fatty compound to the gel matrix; and wherein the composition has a yield point of about 33 Pa or more.

It has been found that by the inventors of the present invention that; by having the above specific conversion rate and the above specific yield point, the hair conditioning compositions deliver improved conditioning benefits, especially improved wet conditioning benefits after rinsing and improved dry conditioning, while maintaining wet conditioning benefit before rinsing, compared to compositions having a smaller conversion rate and/or smaller yield point.

Additionally, it has been also found that by the inventors of the present invention that; by having the above specific conversion rate and the specific yield point, the conditioning composition of the present invention may provide an improved product appearance, i.e., richer, thicker, and/or more concentrated product appearance.

For forming the composition of the present invention, it is preferred to prepare the composition by the method described below under the title "METHOD OF MANUFACTURING". For forming the composition of the present invention, it is also preferred that the total amount of the cationic surfactant and the high melting point fatty compound is from about 7.0%, as described below under the title "METHOD OF MANUFACTURING".

Gel Matrix

The composition of the present invention comprises a gel matrix including lamella gel matrix. The gel matrix comprises the cationic surfactant, the high melting point fatty compound, and an aqueous carrier. The gel matrix is suitable for providing various conditioning benefits, such as slippery feel during the application to wet hair and softness and moisturized feel on dry hair.

In view of providing improved wet conditioning benefits, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:4, still more preferably from about 1:2 to about 1:4.

Preferably, in view of stability of the gel matrix, the composition of the present invention is substantially free of anionic surfactants and anionic polymers. In the present invention, "the composition being substantially free of anionic surfactants and anionic polymers" means that: the composition is free of anionic surfactants and anionic polymers; or, if the composition contains anionic surfactants and anionic polymers, the level of such anionic surfactants and anionic polymers is very low. In the present invention, the total level of such anionic surfactants and anionic polymers, if included, 1% or less, preferably 0.5% or less, more preferably 0.1% or less by weight of the composition. Most preferably, the total level of such anionic surfactants and anionic polymers is 0% by weight of the composition.

Conversion Rate of High Melting Point Fatty Compound to Gel Matrix

The composition of the present invention has a conversion rate of the high melting point fatty compound to gel matrix, such rate being in the range of from about 90% to about 100%, preferably from about 95% to about 100%, more preferably above 99% (excluding 99%) to about 100%, in view of providing wet conditioning benefits before rinsing such as spreadability, and also providing wet conditioning benefits after rinsing_and improved dry conditioning benefits.

Such conversion rate is measured by the following equation:

Conversion rate (%)=[Delta $H$ (J/g) of an endothermic peak having a peak top temperature of from about 67° C. to about 75° C./A total delta $H$ (J/g) of all endothermic peaks]×100

Such delta H is detected by differential scanning calorimetry (hereinafter referred to as "DSC") measurement of the composition. Thermal events obtained by DSC measurement describe chemical and physical changes of the scanned sample that involve an enthalpy change or energy gradient when the temperature of the sample is fluctuated. As such, the phase behavior and interaction among components of hair conditioning compositions of the present invention may be understood by their DSC curves. DSC measurement of compositions of the present invention is conducted by Seiko DSC 6000 instrument available from Seiko Instruments Inc. In a typical measurement procedure, a sample is prepared by sealing an appropriate amount of the composition into a container made for DSC measurement and sealed. The weight of the sample is recorded. A blank sample i.e.; an unsealed sample of the same container is also prepared. The sample and blank sample are placed inside the instrument, and run under a measurement condition of from about −50° C. to about 130° C. at a heating rate of from about 1° C./minute to about 10° C./minute. The area of the peaks as identified are calculated and divided by the weight of the sample to obtain the enthalpy change in mJ/mg. The position of the peaks is identified by the peak top position.

In the compositions of the present invention, the DSC curve shows a endothermic peak of, preferably larger than about 3 mJ/mg, more preferably from about 4 mJ/mg, still more preferably from about 5 mJ, and preferably to about 10 mJ/mg, and such peak having a peak top temperature of from about 67° C. to about 75° C. which indicates the existence of a gel matrix. The DSC curve of the compositions of the present invention shows, preferably no peaks larger than 2.5 mJ/mg, more preferably no peaks larger than 2 mJ/mg, still more preferably no peaks larger than 1 mJ/mg, at a temperature of from 40° C. to 55° C., preferably from 40° C. to about 65° C., as the peaks having peak top temperatures at such temperature range mean the existence of high melting fatty compounds and/or cationic surfactants which are not incorporated into the gel matrix. It is believed that a composition formed predominantly with such a gel matrix shows a relatively stable phase behavior during the temperature range of from about 40° C. to about 55° C., preferably from 40° C. to about 65° C.

Yield Point

The composition of the present invention has a yield point of about 33 Pa or more preferably about 35 Pa or more, more preferably 40 Pa or more, in view of providing improved wet conditioning benefits after rinsing, and improved dry conditioning. The above yield point may be also preferred in view of providing richer, thicker, and/or more concentrated product appearance. Preferably, the yield point is up to about 80 Pa, more preferably up to about 75 Pa, still more preferably up to about 70 Pa, in view of spreadability and product appearance.

The yield point of the present invention is measured by dynamic oscillation stress sweep at 1 Hz frequency and 25° C., by means of a rheometer available from TA Instruments with a mode name of AR2000 using 40 mm diameter parallel type geometry having gap of 1000 m.

Preferably, in view of spreadability, the composition of the present invention is substantially free of thickening polymers. In the present invention, "the composition being substantially free of thickening polymers" means that: the composition is free of thickening polymers; or, if the composition contains a thickening polymer, the level of such thickening polymer is very low. In the present invention, the level of such thickening polymers, if included, 1% or less, preferably 0.5% or less, more preferably 0.1% or less, still more preferably 0.06% by weight of the composition. Such thickening polymers include, for example, guar polymers including nonionic and cationic guar polymers, cellulose polymers including nonionic, cationic, and/or hydrophobically modified cellulose polymers such as cetyl hydroxyethylcellulose, other synthetic polymers including nonionic and cationic synthetic polymers such as polyquaternium-37.

D-Spacing

Figure 1:
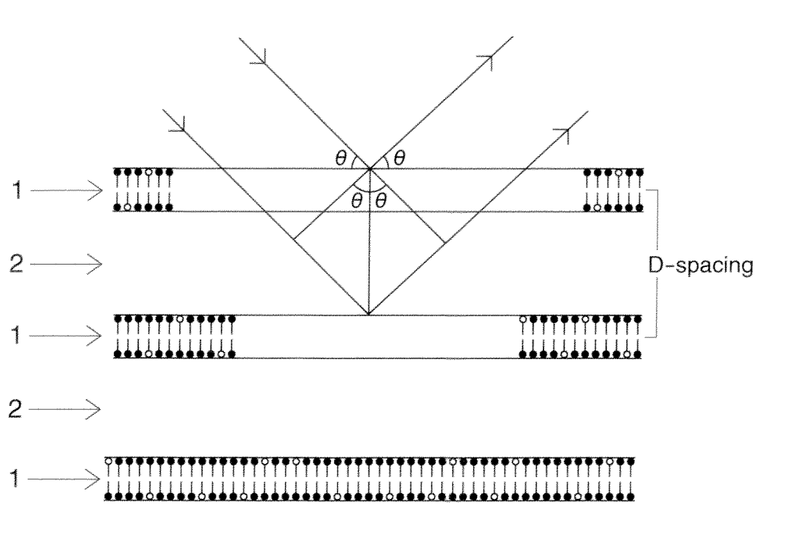
FIG. 1 illustrates an embodiment of d-spacing measurement of the lamellar gel matrix comprising lamella bilayers 1 and water 2.

It has been surprisingly found by the inventors of the present invention that; compositions characterized by the combination of the above specific conversion rate and specific yield point provide improved wet performance, especially wet conditioning after rinsing, even if such compositions having a larger d-spacing than those of the compositions of WO 2006/044209. Such larger d-spacing herein means a d-spacing of above 33 nm (excluding 33 nm). D-spacing in the present invention means a distance between two lamellar bilayers plus the width of one lamellar bilayer, in lamellar gel matrix, as shown in FIG. 1. Thus, d-spacing is defined according to the following equation:

$$D\text{-spacing} = d_{water} + d_{bilayer}$$

D-spacing can be measured by using a High Flux Small Angle X-ray Scattering Instrument available from PANalytical with a tradename SAXSess, under the typical conditions of Small Angle X-Ray Scattering (SAXS) measurements in a q-range ($q=4\pi/\lambda \sin(\theta)$ wherein $\lambda$, is the wavelength and $\theta$ is half the scattering angel) of $0.06 < q/\text{nm}^{-1} < 27$ which corresponds to $0.085 < 2\theta/\text{degree} < 40$. All data are transmission-calibrated by monitoring the attenuated primary beam intensity and normalizing it into unity, so that relative intensity for different samples can be obtained. The transmission-calibration allows us to make an accurate subtraction of water contribution from the net sample scattering. D-spacing is calculated according to the following equation (which is known as Bragg's equation):

$$n\lambda = 2d \sin(\theta), \text{ wherein } n \text{ is the number of lamellar bi-layers}$$

Cationic Surfactant

The compositions of the present invention comprise a cationic surfactant. The cationic surfactant can be included in the composition at a level from about 1%, preferably from about 1.5%, more preferably from about 1.8%, still more preferably from about 2.0%, and to about 8%, preferably to about 5%, more preferably to about 4% by weight of the composition, in view of providing the benefits of the present invention.

It is preferred in the present invention that, in view of improved wet conditioning benefits, the composition is substantially free of other cationic surfactants than those preferred in the present invention. Such "other cationic surfactant" includes, for example, tertiary amines, tertiary amine salts, and di-long alkyl cationic surfactants having two long alkyl chains, for example those having from about 12 to about 40 carbon atoms, such as dicetyl dimethyl ammonium chloride and distearyl dimethyl ammonium chloride. In the present invention, "the composition being substantially free of other cationic surfactants" means that: the composition is free of other cationic surfactants; or, if the composition contains other cationic surfactants, the level of such other cationic surfactants is very low. In the present invention, the level of such other cationic surfactants, if included, 1% or less, preferably 0.5% or less, more preferably 0.1% or less by weight of the composition. Most preferably, the level of such other cationic surfactants is 0% by weight of the composition.

Mono-Long Alkyl Quaternized Ammonium Salt Cationic Surfactant

One of the preferred cationic surfactants of the present invention is a salt of a mono-long alkyl quaternized ammonium and an anion, wherein the anion is selected from the group consisting of halides such as chloride and bromide, C1-C4 alkyl sulfate such as methosulfate and ethosulfate, and mixtures thereof. More preferably, the anion is selected from the group consisting of halides such as chloride and mixtures thereof.

The mono-long alkyl quaternized ammonium salts useful herein are those having the formula (I):

wherein one of $R^{71}$, $R^{72}$, $R^{73}$ and $R^{74}$ is selected from an aliphatic group of from 12 to 40 carbon atoms or an aromatic, alkoxy, polyoxyalkylene, alkylamido, hydroxyalkyl, aryl or alkylaryl group having up to about 40 carbon atoms; the remainder of $R^{71}$, $R^{72}$, $R^{73}$ and $R^{74}$ are independently selected from an aliphatic group of from 1 to about 8 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, one of $R^{71}$, $R^{72}$, $R^{73}$ and $R^{74}$ is selected from an alkyl group of from 16 to 40 carbon atoms, more preferably from 18 to 26 carbon atoms, still more preferably from 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof. It is believed that such mono-long alkyl quaternized ammonium salts can provide improved slippery and slick feel on wet hair, compared to multi-long alkyl quaternized ammonium salts. It is also believed that mono-long alkyl quaternized ammonium salts can provide improved hydrophobicity and smooth feel on dry hair, compared to amine or amine salt cationic surfactants.

Among them, more preferred cationic surfactants are those having a longer alkyl group, i.e., C18-22 alkyl group. Such cationic surfactants include, for example, behenyl trimethyl ammonium chloride, methyl sulfate or ethyl sulfate, and stearyl trimethyl ammonium chloride, methyl sulfate or ethyl sulfate. Further preferred are behenyl trimethyl ammonium chloride, methyl sulfate or ethyl sulfate, and still further preferred is behenyl trimethyl ammonium chloride. It is believed that; cationic surfactants having a longer alkyl group provide improved deposition on the hair, thus can provide improved conditioning benefits such as improved softness on dry hair, compared to cationic surfactant having a shorter alkyl group. It is also believed that such cationic surfactants can provide reduced irritation, compared to cationic surfactants having a shorter alkyl group.

High Melting Point Fatty Compound

The high melting point fatty compound can be included in the composition at a level of from about 2%, preferably from about 4%, more preferably from about 5%, still more preferably from about 5.5%, and to about 15%, preferably to about 10% by weight of the composition, in view of providing the benefits of the present invention.

The high melting point fatty compound useful herein have a melting point of 25° C. or higher, preferably 40° C. or higher, more preferably 45° C. or higher, still more preferably 50° C. or higher, in view of stability of the gel matrix. Preferably, such melting point is up to about 90° C., more preferably up to about 80° C., still more preferably up to about 70° C., even more preferably up to about 65° C., in view of easier manufacturing and easier emulsification. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols.

Preferred fatty alcohols include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present invention, more preferred fatty alcohols are cetyl alcohol, stearyl alcohol and mixtures thereof.

Commercially available high melting point fatty compounds useful herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan).

Aqueous Carrier

The conditioning composition of the present invention comprises an aqueous carrier. The level and species of the carrier are selected according to the compatibility with other components, and other desired characteristic of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 30% to about 95%, and more preferably from about 80% to about 90% water.

Silicone Compound

Preferably, the compositions of the present invention preferably contain a silicone compound. It is believed that the silicone compound can provide smoothness and softness on dry hair. The silicone compounds herein can be used at levels by weight of the composition of preferably from about 0.1% to about 20%, more preferably from about 0.5% to about 10%, still more preferably from about 1% to about 8%.

Preferably, the silicone compounds have an average particle size of from about 1 microns to about 50 microns, in the composition.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quatemized silicones, and mixtures thereof. Other nonvolatile silicone compounds having conditioning properties can also be used.

Preferred polyalkyl siloxanes include, for example, polydimethylsiloxane, polydiethylsiloxane, and polymethylphenylsiloxane. Polydimethylsiloxane, which is also known as dimethicone, is especially preferred. These silicone compounds are available, for example, from the General Electric Company in their Viscasil® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

Silicone compounds useful herein also include amino substituted materials. Preferred aminosilicones include, for example, those which conform to the general formula (I):

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: —N($R_2$)$CH_2$—$CH_2$—N($R_2$)$_2$; —N($R_2$)$_2$; —N($R_2$)$_3$$A^-$; —N($R_2$)$CH_2$—$CH_2$—$NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

Highly preferred amino silicones are those corresponding to formula (I) wherein m=0, a=1, q=3, G=methyl, n is preferably from about 1500 to about 1700, more preferably about 1600; and L is —N(CH3)2 or —NH2, more preferably —NH2. Another highly preferred amino silicones are those corresponding to formula (I) wherein m=0, a=1, q=3, G=methyl, n is preferably from about 400 to about 600, more preferably about 500; and L is —N(CH3)2 or —NH$_2$, more preferably —NH$_2$. Such highly preferred amino silicones can be called as terminal aminosilicones, as one or both ends of the silicone chain are terminated by nitrogen containing group.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning.

The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; coloring agents, such as any of the FD&C or D&C dyes; perfumes; and sequestering agents, such as disodium ethylenediamine tetra-acetate; ultraviolet and infrared screening and absorbing agents such as benzophenones; and antidandruff agents such as zinc pyrithione.

Low Melting Point Oil

Low melting point oils useful herein are those having a melting point of less than 25° C. The low melting point oil useful herein is selected from the group consisting of: hydrocarbon having from 10 to about 40 carbon atoms; unsaturated fatty alcohols having from about 10 to about 30 carbon atoms such as oleyl alcohol; unsaturated fatty acids having from about 10 to about 30 carbon atoms; fatty acid derivatives; fatty alcohol derivatives; ester oils such as pentaerythritol ester oils including pentaerythritol tetraisostearate, trimethylol ester oils, citrate ester oils, and glyceryl ester oils; poly α-olefin oils such as polydecenes; and mixtures thereof.

Product Forms

The conditioning compositions of the present invention can be in the form of rinse-off products or leave-on products, and can be formulated in a wide variety of product forms, including but not limited to creams, gels, emulsions, mousses and sprays. The conditioning composition of the present invention is especially suitable for rinse-off hair conditioner.

Method of Use

The conditioning composition of the present invention is preferably used for a method of conditioning hair, the method comprising following steps:
(i) after shampooing hair, applying to the hair an effective amount of the conditioning composition for conditioning the hair; and
(ii) then rinsing the hair.

Effective amount herein is, for example, from about 0.1 ml to about 2 ml per 10 g of hair, preferably from about 0.2 ml to about 1.5 ml per 10 g of hair.

The conditioning composition of the present invention provides improved conditioning benefits, especially improved wet conditioning benefits after rinsing and improved dry conditioning, while maintaining wet conditioning benefit before rinsing. The conditioning composition of the present invention may also provide improved product appearance to consumer. Thus, a reduced dosage of the conditioning composition of the present invention may provide the same level of conditioning benefits as those of a full dosage of conventional conditioner compositions. Such reduced dosage herein is, for example, from about 0.3 ml to about 0.7 ml per 10 g of hair.

Method of Manufacturing

The present invention is also directed to a method of manufacturing a hair conditioning composition, wherein the composition comprises a cationic surfactant, a high melting point fatty compound, and an aqueous carrier; wherein a total amount of the cationic surfactant and the high melting point fatty compound is from about 7.0% to about 15% by weight of the composition;
wherein the method comprises the steps:
(1) preparing a premix (hereinafter, can be referred to as oil phase) comprising the cationic surfactants and the high melting point fatty compounds, wherein the temperature of the premix is higher than a melting point of the high melting point fatty compounds; and
(2) preparing an aqueous carrier (hereinafter, can be referred to as aqueous phase), wherein the temperature of the aqueous carrier is below the melting point of the high melting point fatty compounds; and
(3) mixing the premix with the aqueous carrier and forming gel matrix.

Preferably, the method further comprises the step of adding additional ingredients such as silicone compounds, perfumes, preservatives, if included, to the gel matrix.

Preferably, the premix has a temperature of from about 25° C., more preferably from about 40° C., still more preferably from about 50° C., even more preferably from about 55° C., further preferably from about 65° C., and to about 150° C., more preferably to about 95° C., still more preferably to about 90° C., even more preferably to about 85° C., when mixing it with the aqueous carrier.

Preferably, the aqueous carrier has a temperature of from about 10° C., more preferably from about 15° C., still more preferably from about 20° C., and to about 65° C., more preferably to about 55° C., still more preferably to about 52° C., when mixing it with the premix. Preferably, the temperature of the aqueous carrier, when mixing it with the premix, is at least about 5° C. lower than, more preferably at least about 10° C. lower than the temperature of the premix. Preferably, the temperature of the aqueous carrier, when mixing it with the premix, is from about 2° C. to about 60° C. lower than, more preferably from about 2° C. to about 40° C. lower than, still more preferably from about 2° C. to about 30° C. lower than the melting point of the high melting point fatty compounds.

Preferably, the premix and the aqueous carrier are mixed by using a high shear homogenizer. Such high shear homogenizers useful herein include, for example: Sonolator® available from Sonic Corporation, Manton Gaulin type homogenizer available from the APV Manton Corporation, the Microfluidizer available from Microfluidics Corporation, Becomix® available from A. Berents Gmbh&Co.

Preferably, the total amount of the cationic surfactant and the high melting point fatty compound is from about 7.0%, preferably from about 7.5%, more preferably from about 8.0% by weight of the composition, in view of providing the benefits of the present invention, and to about 15%, preferably to about 14%, more preferably to about 13%, still more preferably to about 10% by weight of the composition, in view of spreadability and product appearance.

Preferably, the mixing step (3) comprises the following detailed steps: (3-1) feeding either of the oil phase or the aqueous phase into a high shear field having an energy density of about $1.0 \times 10^2$ J/m$^3$ or more; (3-2) feeding the other phase directly to the field; and (3-3) forming an emulsion. Preferably, the method further requires at least one of the following: the mixing step (3) is conducted by using a homogenizer having a rotating member; the surfactant is a mono-alkyl cationic surfactant and the composition is substantially free of di-alkyl cationic surfactants; and the surfactant is a cationic surfactant and the oil phase contains from 0 to about 50% of the aqueous carrier by weight of the oil phase, preferably the oil phase is substantially free of water.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

| Compositions (wt %) | | | | | | | |
|---|---|---|---|---|---|---|---|
| Components | Ex. 1 | Ex. 2 | Ex. 3 | Ex. 4 | Ex. i | Ex. ii | Ex. iii |
| Behenyl trimethyl ammonium chloride | 2.3 | 2.8 | 3.4 | — | 2.8 | 2.8 | 1.8 |
| Behenyl trimethyl ammonium methyl sulfate | — | — | — | 2.8 | — | — | — |
| Cetyl alcohol | 1.5 | 1.9 | 2.2 | 1.9 | 1.9 | 1.9 | 1.2 |
| Stearyl alcohol | 3.7 | 4.7 | 5.5 | 4.6 | 4.7 | 4.7 | 2.9 |
| Aminosilicone *1 | 1.5 | 1.5 | 1.5 | 1.5 | 1.5 | 1.5 | 1.5 |
| Isopropanol | — | 0.6 | — | 0.6 | — | — | — |
| Dipropylene glycol | — | — | 0.7 | — | — | — | — |
| Cetyl hydroxyethyl cellulose *2 | — | — | — | — | 0.5 | — | — |
| Disodium EDTA | 0.13 | 0.13 | 0.13 | 0.13 | 0.13 | 0.13 | 0.13 |
| Preservatives | 0.4 | 0.4 | 0.4 | 0.4 | 0.4 | 0.4 | 0.4 |
| Perfume | 0.35 | 0.35 | 0.35 | 0.35 | 0.35 | 0.35 | 0.35 |
| Panthenol | 0.05 | 0.05 | 0.05 | 0.05 | 0.05 | 0.05 | 0.05 |
| Panthenyl ethyl ether | 0.03 | 0.03 | 0.03 | 0.03 | 0.03 | 0.03 | 0.03 |
| Deionized Water | q.s. to 100% | | | | | | |

Definitions of Components
*1 Aminosilicone: Available from GE having a viscosity 10,000 mPa · s, and having following formula (I): $(R_1)_a G_{3-a}$—Si—$(—OSiG_2)_n$—$(—OSiG_b(R_1)_{2-b})_m$—O—$SiG_{3-a}(R_1)_a$ (I) wherein G is methyl; a is an integer of 1; b is 0, 1 or 2, preferably 1; n is a number from 400 to about 600; m is an integer of 0; $R_1$ is a monovalent radical conforming to the general formula $CqH_{2q}L$, wherein q is an integer of 3 and L is —$NH_2$
*2 Cetyl hydroxyethyl cellulose: Polysurf available from Hurcules Inc.

Method of Preparation

The conditioning compositions of "Ex. 1" through "Ex. 4" and the composition of "Ex. iii" are suitably made as follows:
Cationic surfactants and high melting point fatty compounds are mixed and heated to from about 65° C. to about 90° C. to form a premix. Separately, water is prepared at from about 25° C. to about 52° C. In Becomix® direct injection rotor-stator homogenizer, the premix is injected to a high shear field having an energy density of from $1.0×10^4$ J/m$^3$ to $1.0×10^7$ J/m$^3$ where the water is already present. A gel matrix is formed. If included, silicone compounds, perfumes, preservatives are added to the gel matrix with agitation. Then the composition is cooled down to room temperature.

The conditioning compositions of "Ex. i" and "Ex. ii" as shown above can be prepared by any conventional method well known in the art. They are suitably made as follows: If included, polymers are added to water with agitation. Cationic surfactants and high melting point fatty compounds are added to water with agitation, and heated to about 80° C. The mixture is cooled down to about 55° C. and gel matrix is formed. If included, silicone compounds, perfumes, preservatives are added to the gel matrix with agitation. Then the mixture is cooled down to room temperature.

Properties and Conditioning Benefits

With respect to the above compositions of Ex. 1-4 and Ex. i-iii, the yield stress and the conversion rate are measured by the methods described above. For some of the compositions, d-spacing is also measured by the method described above. Such properties of the compositions are shown in below Table 1.

With respect to the above compositions of Ex. 1-4 and Ex. i-iii, conditioning benefits are evaluated by the following methods. Results of the evaluation are also shown in below Table 1.

Wet Conditioning Before Rinsing

Wet conditioning before rinsing is evaluated by hair friction force measured by an instrument named Texture Analyzer (TA XT Plus, Texture Technologies, Scarsdale, NY, USA). 1 g of the composition is applied to 10 g of hair sample. After spreading the composition on the hair sample and before rinsing it, friction force (g) between the hair sample and a polyurethane pad is measured by the above instrument.
  A: Above 5% (excluding 5%) to 10% reduction of Friction force, compared to Control
  B: Up to 5% (including 5%) reduction of Friction force, compared to Control
  C: Control or Equal to Control
  D: Increased Friction force, compared to Control Wet Conditioning After Rinsing Wet conditioning after rinsing is evaluated by hair friction force measured by an instrument named Texture Analyzer (TA XT Plus, Texture Technologies, Scarsdale, N.Y., USA). 1 g of the composition is applied to 10 g of hair sample. After spreading the composition on the hair sample, rinsing it with warm water for 30 seconds. Then, friction force (g) between the hair sample and a polyurethane pad is measured by the above instrument.
  A: Above 5% (excluding 5%) to 10% reduction of Friction force, compared to Control
  B: Up to 5% (including 5%) reduction of Friction force, compared to Control
  C: Control or Equal to Control
  D: Increased Friction force, compared to Control Dry Conditioning Dry conditioning performance is evaluated by hair friction force measured by an instrument named Instron Tester (Instron 5542, Instron, Inc; Canton, Mass., USA). 2 g of the composition is applied to 20 g of hair sample. After spreading the composition on the hair sample, rinsing it with warm water for 30 seconds, and the hair sample is left to dry overnight. The friction force (g) between the hair surface and a urethane pad along the hair is measured.
  A: Above 5% (excluding 5%) to 10% reduction of Friction force, compared to Control
  B: Up to 5% (including 5%) reduction of Friction force, compared to Control
  C: Control or Equal to Control
  D: Increased Friction force, compared to Control Product Appearance The product appearance is evaluated by 6 panelists, when dispensing 0.4 ml of a conditioner product from a package.
  A: From 3 to 6 panelists answered that the product had a thick product appearance and perceived positive impression from its appearance.

B: From 1 to 2 panelists answered that the product has a thick product appearance and perceived positive impression from its appearance.

C: Control

TABLE 1

|  | Ex. 1 | Ex. 2 | Ex. 3 | Ex. 4 | Ex. i | Ex. ii | Ex. iii |
|---|---|---|---|---|---|---|---|
| Yield point | 37 | 47 | 52 | 50 | >33 | 25 | 16 |
| Conversion rate of High melting point fatty compounds to Gel matrix | 100 | 100 | 100 | 100 | <90 | 55 | 100 |
| D-spacing | >50 | >50 | — | — | — | 29 | >50 |
| Wet conditioning before rinsing | A | A | A | A | D | C | B |
| Wet conditioning after rinsing | A | A | A | A | D | C | C |
| Dry conditioning | B | A | A | B | D | C | C |
| Product appearance | A | A | B | — | — | C | — |

The embodiments disclosed and represented by the previous "Ex. 1" through "Ex. 4" are hair conditioning compositions of the present invention which are particularly useful for rinse-off use. Such embodiments have many advantages. For example, they provide improved conditioning benefits, especially improved wet conditioning benefits after rinsing and improved dry conditioning, while maintaining wet conditioning benefit before rinsing.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing a hair conditioning composition, wherein the hair conditioning composition comprises from about 1% to about 8% of a cationic surfactant selected from the group consisting of behenyl trimethyl ammonium chloride, behenyl trimethyl ammonium methyl sulfate, behenyl trimethyl ammonium ethyl sulfate, stearyl trimethyl ammonium chloride, and combinations thereof, from about 2% to about 10% of a fatty alcohol selected from the group consisting of stearyl alcohol, cetyl alcohol, behenyl alcohol, and mixtures thereof, and an aqueous carrier; wherein the hair conditioning composition comprises from about 7.5% to about 10% cationic surfactant and fatty alcohol combined, by weight of the hair conditioning composition;

wherein the method comprises the steps:
(1) preparing an oil phase comprising the cationic surfactants and the fatty alcohol, wherein the temperature of the oil phase is higher than a melting point of the fatty alcohol; and
(2) preparing an aqueous phase, wherein the temperature of the aqueous phase is below the melting point of the fatty alcohol; and
(3) mixing the oil phase with the aqueous phase and forming a gel matrix;

wherein the mixing step (3) comprises the steps:
(3-1) feeding either of the oil phase or the aqueous phase into a high shear field having an energy density of about $1.0 \times 10^2$ J/m$^3$ or more;
(3-2) feeding the other phase directly to the field; and
(3-3) forming the gel matrix;

wherein the oil phase has a temperature of from about 65° C. to about 95° C. when mixing it with the aqueous phase;
wherein the aqueous phase has a temperature of from about 10° C. to about 52° C. when mixing it with the oil phase;
wherein the temperature of the aqueous phase, when mixing it with the oil phase, is from about 2° C. to about 60° C. lower than the melting point of the fatty alcohol;
wherein the hair conditioning composition is free of di-alkyl cationic surfactants;
wherein the oil phase and the aqueous phase are mixed by a high shear homogenizer;
wherein the oil phase comprises from 0% to about 50% of an aqueous carrier by weight of the oil phase.

2. The method of manufacturing of claim 1, wherein the oil phase is free of water.

3. The method of manufacturing of claim 1, wherein the high shear field has an energy density of from about $1.0 \times 10^4$ J/m$^3$ to about $1.0 \times 10^7$ J/m$^3$.

4. The method of manufacturing of claim 1, wherein the aqueous carrier is selected from the group consisting of water, solutions of lower alkyl alcohols, polyhydric alcohols, and combinations thereof.

5. The method of manufacturing of claim 1, wherein the fatty alcohol is selected from the group consisting of stearyl alcohol, cetyl alcohol, and mixtures thereof.

6. The method of manufacturing of claim 1, wherein the cationic surfactant is selected from the group consisting of behenyl trimethyl ammonium chloride, behenyl trimethyl ammonium methyl sulfate, and combinations thereof.

7. The method of manufacturing of claim 1, wherein the hair conditioning composition has from about 90% to about 100% of a conversion rate of the fatty alcohol to the gel matrix.

8. The method of manufacturing of claim 1, wherein the hair conditioning composition has from about 95% to about 100% of a conversion rate of the fatty alcohol to the gel matrix.

9. The method of manufacturing of claim 1, wherein the hair conditioning composition has from greater than 99% of a conversion rate of the fatty alcohol to the gel matrix.

10. The method of manufacturing of claim 1, wherein the cationic surfactant is behenyl trimethyl ammonium methyl sulfate.

* * * * *